United States Patent [19]

Boyer et al.

[11] Patent Number: 4,480,920

[45] Date of Patent: Nov. 6, 1984

[54] FRINGE PATTERN METHOD AND APPARATUS FOR PRODUCING X-RAY DOSAGE COMPENSATING FILTERS

[75] Inventors: Arthur L. Boyer, New Braunsfels, Tex.; Michael Goitein, Belmont, Mass.

[73] Assignee: The Massachusetts General Hospital Corporation, Boston, Mass.

[21] Appl. No.: 519,216

[22] Filed: Aug. 2, 1983

Related U.S. Application Data

[63] Continuation of Ser. No. 190,250, Sep. 24, 1980.

[51] Int. Cl.³ .................................................. G01B 11/24
[52] U.S. Cl. ..................................................... 356/376
[58] Field of Search .................................. 356/376, 2

[56] References Cited

U.S. PATENT DOCUMENTS 2,759,814  8/1956  Kegeles .................................. 356/2
3,614,237  10/1971  Kyle et al. ........................... 356/376

OTHER PUBLICATIONS

Fujita et al., "Moire Topographic Technique Applied to Design of Compensator for Telecobalt Therapy", *Japanese Medical Radiology Academy Magazine*, vol. 34, No. 6, (Jun. 25, 1974), pp. 416–417.
Keck et al., "Moiré-Topographische Verfahren in der Medizin: Anwendung in der Strahlentherapie", *Optik*, 46, (1976), No. 4, 431–437.
Xenofos et al., "Theoretical Aspects and Practical Applications of Moiré Topography", *Phys. Med. Biol.*, 1979, vol. 24, No. 2, 250–261.

*Primary Examiner*—R. A. Rosenberger
*Attorney, Agent, or Firm*—Weingarten, Schurgin, Gagnebin & Hayes

[57] ABSTRACT

Method and apparatus for producing a fringe pattern corresponding to height and depth gradients of an illuminated object with the fringe pattern lines used to define edges of stacked sheets provided as a filter for X-ray dosage tailoring. A camera is provided to produce the fringe pattern on a photographic film using a compact arrangement of light sources, lenses and gratings all within a convenient housing facilitating use yet at the same time providing sufficient resolution through separation of projection and imaging optics. A laser range finder is additionally provided to insure placement of the object to be X-rayed, typically a portion of the human torso, at a standard distance so that the ultimately produced X-ray filter will be properly sized. The filter is produced by cutting a set of lead sheets with edges corresponding to each of the separate contour lines in the exposed and developed film receiving the fringe pattern. Projection techniques are employed in order to size the film record of fringe patterns to a size appropriate for use as an X-ray filter, typically less than life size.

6 Claims, 13 Drawing Figures

FIG. 5
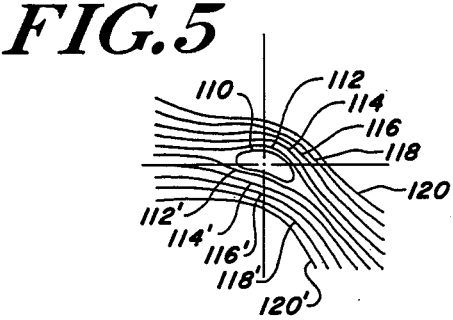
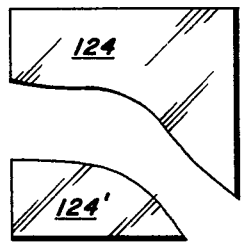
FIG. 6A
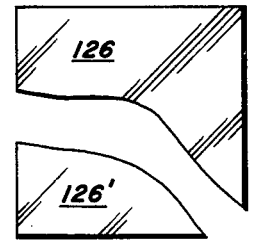
FIG. 6B
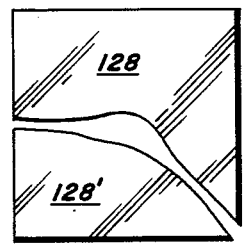
FIG. 6C
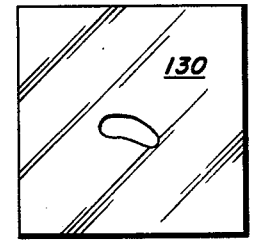
FIG. 6D
FIG. 6E
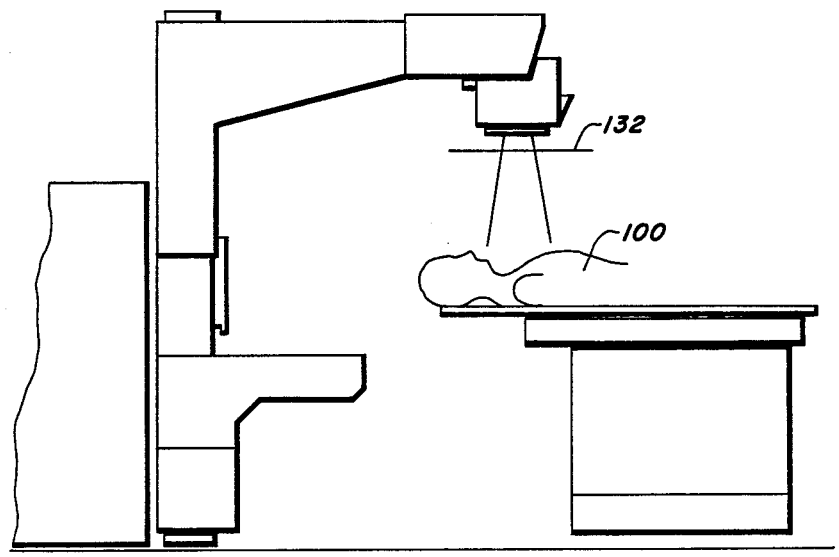
FIG. 7

FRINGE PATTERN METHOD AND APPARATUS FOR PRODUCING X-RAY DOSAGE COMPENSATING FILTERS

This application is a continuation of application Ser. No. 190,250, filed Sept. 24, 1980.

FIELD OF THE INVENTION

The present invention relates to fringe or moire pattern cameras and techniques for developing X-ray exposure filters from the photographed fringe pattern.

BACKGROUND OF THE INVENTION

It is frequently desired to adjust the intensity of an X-ray beam applied to regions of the human torso in accordance with the actual tissue thickness, or missing tissue, in the body across the lateral dimensions of the X-ray beam. This results in a more uniform tissue dosage to avoid excessive X-ray exposure and to provide a more uniform exposure pattern.

In order to adjust the intensity of an X-ray beam applied to a portion of the human torso a filter can be developed, typically consisting of a stacked set of lead sheets each cut in accordance with a predetermined contour depth of the torso being irradiated. In order to cut the sheets a knowledge of the relative height, along the radiation exposure axis, of the body portion being illuminated is required. This has been practiced in the prior art by techniques of physical dimension gaging using a set of rods or the more cumbersome technique of actually taking a plaster cast of the patient torso. In addition a technique has been used whereby a series of parallel grid lines have been projected onto the object from an angle orthogonal to the X-ray exposure position. Finally, various techniques of photogrammetry and computer processing have been used in the past to develop the surface gradient topography for use in generating a filter. In addition the use of moire patterns resulting from the fringing or interference of two grid lines has been investigated as a means for topography measurement of the human body, see for example the article by the inventor in Volume 7 No. 1, Journal of Medical Physics pp 19-29, 1980.

BRIEF SUMMARY OF THE INVENTION

In the present invention a compact and effective camera system is provided for generating moire pattern photographic images from which, by suitable projection, a set of patient contours in nearly life size relationship can be provided that greatly simplify the cutting of filter sheets for controlling X-ray dosage in accordance with tissue depth.

A camera is provided for generating on film a developable photographic image of the fringe pattern with each fringe ring representing a predetermined difference in distance from the camera cooresponding to object gradient lines. The camera includes a laser range finder to permit precise positioning of the patient for a predetermined camera-to-patient distance. First and second lenses of high linearity are provided, the first to image a set of grating lines illuminated by a flashlamp onto the object or patient and the second to focus the thus imaged grating lines through a second grating to produce a moire interference pattern on the film. The exposed and developed film is then projected to a predetermined enlargement scale, typically corresponding to less than life size. Sheets of lead are then cut in correspondence with each of the fringe lines or intermediate lines on the projected pattern and the separate sheets are assembled in registration to provide a step gradation in lead thickness over the filter to adjust X-ray dosage according to tissue thickness. The filter is then placed over the patient in line with the original fringe pattern before application of the X-ray energy.

BRIEF DESCRIPTION OF THE DRAWING

These and other features of the present invention are more fully set forth below in the detailed description of the disclosure and the accompanying drawing of which:

FIG. 5 is a hypothetical moire pattern produced by the camera of the present invention as installed in the view of FIG. 4;

FIGS. 6A-6E show a set of lead plates cut in accordance with the moire pattern of FIG. 5;

FIG. 7 is a view of the apparatus of FIG. 4 in use to expose a patient to X-ray radiation through a filter formed through assemblage of the sheets of FIGS. 6A-6E.

DETAILED DESCRIPTION OF THE DISCLOSURE

The present invention contemplates a system for generating an X-ray dosage filter to compensate for varying tissue thicknesses exposed to X-ray radiation. A compact camera system is provided for generating moire fringe pattern images providing gradient lines of object or patient topography and an enlargement technique is provided for forming a set of lead sheets corresponding in outline to the fringe pattern rings whereby an X-ray exposure filter can be developed.

Figure 1:
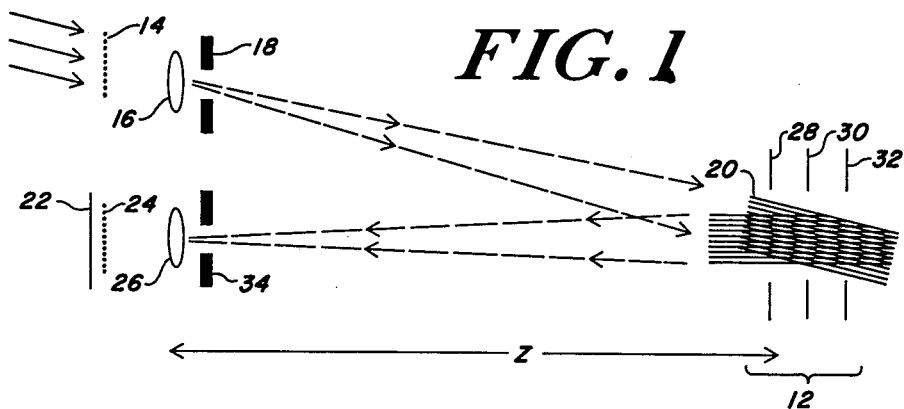
FIG. 1 is a diagrammatic representation of the principle of operation of the camera in accordance with the present invention.

With reference to FIG. 1, a diagrammatic view is shown of the camera principle for exposing a film with a moire fringe pattern revealing the topography in gradient lines of an object located at a position 12. Light is directed toward the position 12 through a grating 14 and imaged by a lens 16 through an aperture 18 to provide a series of parallel bands 20 of radiation varying in intensity from a high intensity sheet to a relatively low intensity sheet in the region 12. Effectively the lens 16 is operative to image the grating 14 to the region 12 with a substantial depth of field so as to produce the effect of a series of parallel slabs of periodically varying intensity.

A film plate 22 is provided substantially in a plane parallel to the grating 14 and has directly above it a second grating 24 with its lines substantially parallel to those of the grating 14. A second lens 26 is placed so as to image the region 12 onto the film plate 22. The effect of exposing the film plate 22 through the grating 24 is to generate a series of planes 28, 30 and 32 orthogonal to the central optical axis of the lens 26 which define either maxima or minima intensity planes as perceived at the film plane 22. That is, with proper alignment as discussed below, the image plane 22 will view each of the fringe planes 28, 30 and 32 as a constant intensity maxima or minima. With an object of complex topography placed in the location 12 and facing the lens 26 behind the aperture 34, the various planes, 28, 30 and 32 will appear as fringe lines of a moire pattern upon the surface of the object as imaged in the plane 22. These fringe lines will designate lines of constant distance from the film plate 22. The distance between the planes 28, 30 and 32 can be measured imperically, or, knowing the geometry of the apparatus of FIG. 1, calculated. For small variations in distance along the optical axis of lens 26 in the region 12 the distance between the fringe lines will remain a constant number thereby permitting a determination of the reduction in tissue thickness, fringe line by fringe line, in the image formed at the film plate 22 after development.

In order for the accuracy of the imaging technique, illustrated in FIG. 1, to be maintained sufficiently to produce dosage compensating filters, the lenses 16 and 26 are identical in power and placed with axes parallel. Lenses 16 and 26 are also substantially linear and distortion free in magnification since the lens 26 is preferably located with its optical axis directly through the region 12 while the lens 16, located parallel in optical axis to the lens 26 provides light at an off axis direction to the region 12. It is therefore important that the magnification remain the same off axis in the lens 16 within the region 12. While other geometries may be utilized, the geometry of FIG. 1 simplifies calculations and insures the accuracy of the filter produced therefrom.

Figure 2A:
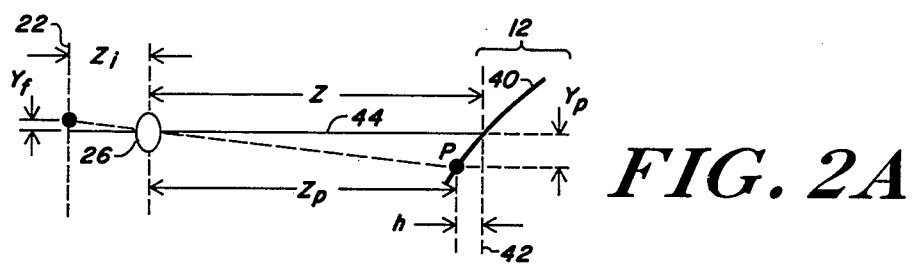
FIGS. 2A-2C are graphical representations of the steps in the process of filter generation in accordance with the present invention.
Figure 2B:
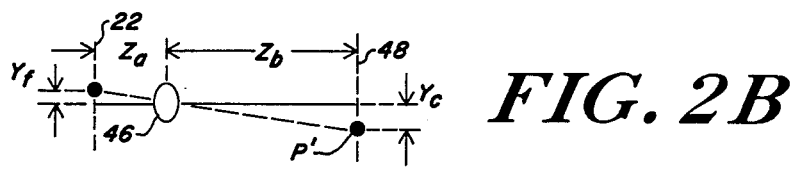
Figure 2C:
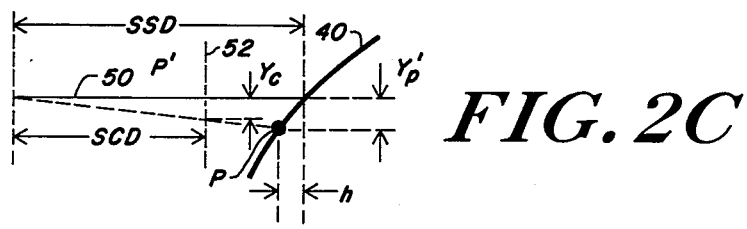

With relation to FIGS. 2A-2C the geometries of the process of filter generation from the moire pattern exposure technique of FIG. 1 may be understood. Lens 26 images an object 40 onto the film plane 22 with a reference plane 42 of the object located a distance Z from the center of the lens 26 and with the image plane 22 located a distance Zi from the lens 26. Accordingly a point P which is located a distance Yp from the optical axis 44 of the lens 26 on the object 40 will be imaged to the plane 22 a distance Yf from the object axis 44 in accordance with conventional optical imaging rules. The exposed and developed film at the plate 22 then is projected through a lens 46 onto a plane 48 a distance Zb from lens 46 which is a fraction of the original distance Z. A shorter projection distance is utilized in order to permit placement of the resulting filter a predetermined distance from the patient for the avoidance of undesired effects from surface dose buildup. The lens 46 is chosen with a power in relation to the lens 26 so that an enlargement of the film in plane 22 will be made to this corresponding lower scale than the original scale of the object 40. The image presented on the surface 48 can then be used for scribing lines directly onto lead sheets which are then cut at the scribe lines and stacked to provide an exposure gradient filter for ultimate X-ray exposure. As illustrated in FIG. 2C, the optical axis 50 of the X-ray exposure passes through a filter plane 52 at which the resulting composite filter is placed thereby imaging to the object 40 the corner of the fringe P' at the identical location P corresponding to its location in FIG. 2A. Given the desired location of the filter plane 52 the geometries of the various lens and source locations may be readily calculated using known optical techniques. In particular the geometries are governed by the equation $$Y_p' = Y_p \times \frac{Z}{Z_p} \times \frac{SPD}{SSD} = Y_p$$

as the desired result.

Figure 3:
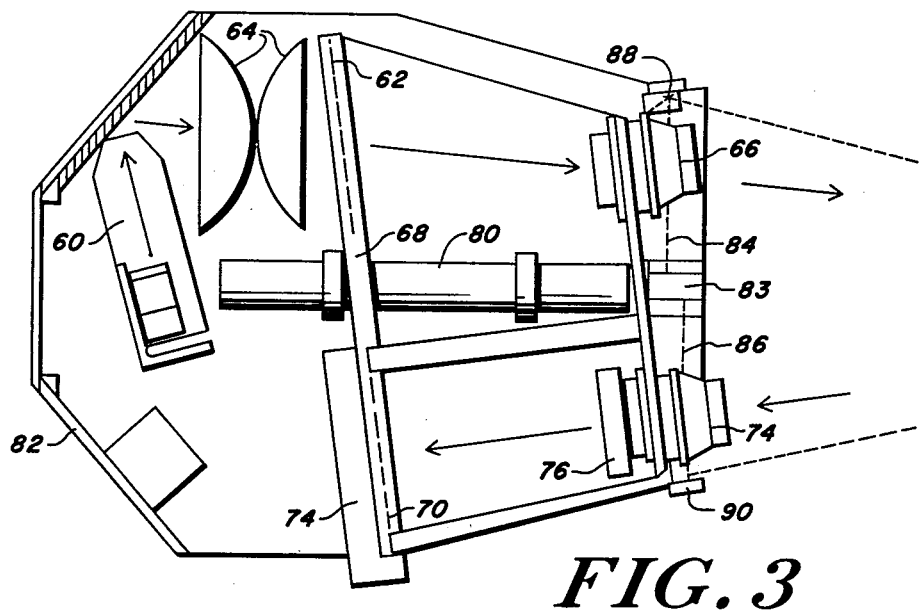
FIG. 3 is a schematic diagram of a camera in accordance with the present invention.

A camera in accordance with the operation of the FIG. 1 diagram is illustrated with respect to FIG. 3. As shown there a light source 60, typically a short duration flashlamp source, provides even illumination across a grating 62 through a condenser lens set 64. The thus illuminated grating 62 is projected through a compound lens 66 onto the object located out of the view of the figure to the right. The resulting projection will be a series of light and dark sheets at the location of the object or patient when an appropriate focal length for the lens 66 is provided. It is preferable that the light source 60 be a straight line source oriented so that its discharge axis is parallel to the lines of grating 62 as projected through the grating by lens set 64. This helps to maintain a large depth of field at the object.

The grating 62 is carried on a bar 68 which, at the other side of the camera of FIG. 3, also contains a substantially identical grating 70 located the same distance along the optical axis from a lens 72, identical in all respects to lens 66. Directly behind the grating 70 is a film holder 74 into which film, such as Polaroid film, may be placed for exposure directly behind the grating 70.

The lenses 66 and 72 will typically include a diaphragm in order to limit the aperture in accordance with the apertures shown at 18 and 34 in FIG. 1. A shutter 76 is also provided to open the light path through the lens 72 to the film in holder 74 only for a brief period during which the flashlamp 60 is activated.

A laser 80 is provided centrally within the housing 82 for the camera and directs a collimated beam of radiation to a beam splitter 83 where it is divided into two separate paths 84 and 86 which are directed by reflectors 88 and 90 to convergence at the desired location for the object or patient. In this manner the patients nearest surface point can be positioned at a predetermined distance from the lenses 66 and 72. Typically this distance should be the same distance from the X-ray source to that position on the object although in practice administering medical technicians will for various reasons wish to vary that distance over a range varying by, for example, a factor of two from say 75 to 150 cm. In order to make a camera system usable within that entire range the laser beam convergence point is set to bring the beams from the reflectors 88 and 90 into coincidence at a distance of 95 cm from the lens 72 as a practical compromise from both extremes. Technically for any filter generated for exposure at a distance other than 95 cm from source to nearest patient point, some error will be generated but within the geometry limits of the camera noted below this error is within the range of tolerance.

In particular, the axes of the lenses 66 and 72 are separated by a distance of 18.4 cm where it is desired that the object distance from the lens 72 be 95 cm. This provides a shallow acute angle between the radiation imaged through the lens 16 and that received by the lens 26 of approximately 11° or 0.2 radians. These dimensions are selected as a matter of convenience in providing a compact camera system and the desire for resolution which increases with lens separation. Using a grating of 80 lines per inch leads to a fringe separation of approximately 6 mm along the optical axis of lens 72 which, by interpolation between fringes can lead to identification of lines of equal distance from the lens 72 within approximately one third of a fringe line or 2 mm. Lens 72 may further have a rectangular aperture rather than the usual circular one to accommodate the rectangular image desired with a maximum depth of field.

Figure 4:
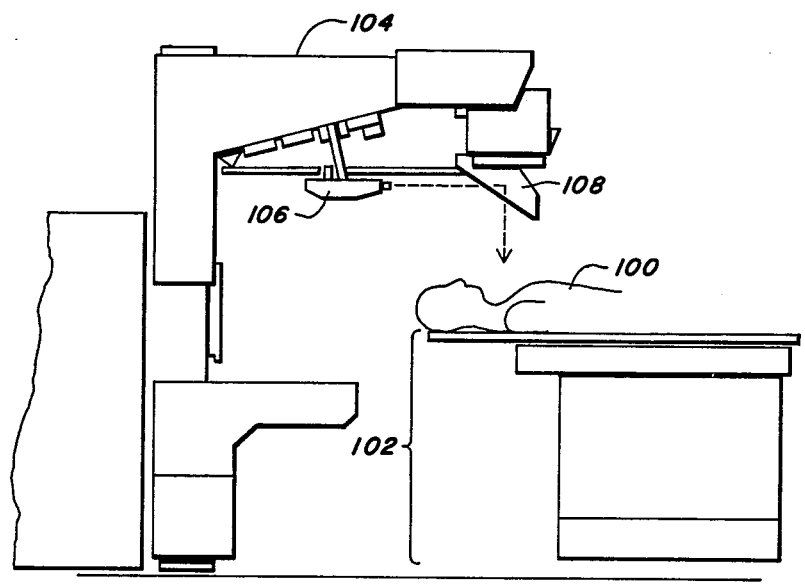
FIG. 4 is a pictorial view of the camera in use on a X-ray machine in accordance with the present invention.

In use the camera of FIG. 3 is typically suspended on a support arm 104 above a patient 100 on a support platform 102 with the camera 106 viewing and illuminating the patient 100 through a mirror 108. (FIG. 4) When thus arranged, the exposed and developed film from the camera 106 will yield a contour pattern hypothetically illustrated in FIG. 5 and showing a set of contour lines 110, 112, 114, 116, 118 and 120 progressing upward in the view of FIG. 5. Contour 110 denotes a position closest to the camera representing maximum tissue thickness while contour 120 reflects a position farthest from the camera and thus minimum tissue thickness. A corresponding set of contour lines 112′, 114′, 116′, 118′ and 120′ progress downward in the field of view of FIG. 5 and reflect progressively increasing distances from the camera and decreasing tissue thickness. When this image is projected as illustrated in FIG. 2B onto a surface 48 a series of lead sheets may be scribed with the locations of the lines 110-120 and 114′-120′ or interpolations between them which, when cut along the scribe lines, will provide a corresponding set of cut lead sheets 122, 122′, 124, 124′, 126, 126′, 128, 128′ and 130 (FIGS. 6A-6E) which correspond in their inner facing edges to the contour lines 120-110 and 120′-114′.

When the sheets of FIGS. 6A-6E are stacked in registration they form a filter 132 illustrated in FIG. 7 which is placed above the patient 100 at the relative locations between patient and source as specified by the enlarging geometry of FIG. 2B and exposure geometry of FIG. 2C in order to achieve the desired compensation.

It should be noted that the above detailed description is specific in many respects, it being contemplated that departures from these exemplary details may be made while still practicing the invention as recited in the following claims.

What is claimed is:

1. A camera for producing an image of fringe lines corresponding to gradient line elevations of an object comprising:
    a camera housing;
    a projection path within said housing including a light source, a first grating illuminated by said light source, and projection means for producing an image of said first grating on said object;
    an imaging path including a second grating parallel to said first grating, imaging means for projecting an image of the object through said second grating; and film holder means for receiving image retaining means adjacent said second grating to receive light from said imaging means after passage through said second grating;
    grating positioning means containing said first and second gratings in substantially side by side relationship within said housing whereby said projection and imaging paths are substantially adjacent to each other within said housing;
    said camera housing adapted to be positioned relative to a radiation source for use in radiation exposure of said object to produce said image of said first grating on said object along the path over which said object is exposed to said radiation; and
    said camera housing having means for holding said first and second gratings in fixed relationship to each other and to said projection and imaging means.

2. The camera of claim 1 further including means for projecting a narrow beam of light along a path substantially between the path of light from said projecting means towards said object and from said object towards said imaging means in order to facilitate positioning of said camera relative to said object.

3. The camera of claim 1 wherein the angle between radiation projected towards said object from said projecting means and receive from said object through said imaging means is a approximately 0.2 radians.

4. The camera of claim 1 wherein said projecting means and said imaging means include lenses having optical axes substantially parallel to each other and orthogonal to said first and second gratings.

5. The camera of claim 1 further including means for supporting said housing in a position to project and receive light vertically from an object when supported on a horizontal platform.

6. A camera for producing an image of fringe lines corresponding to gradient line elevations of an object comprising:
    a camera housing;
    a projection path within said housing including a light source, a first grating illuminated by said light source, and projection means for producing an image of said first grating on said object;
    an imaging path including a second grating parallel to said first grating, imaging means for projecting an image of the object through said second grating; and film holder means for receiving image retaining means adjacent said second grating to receive light from said imaging means after passage through said second grating;
    grating positioning means containing said first and second gratings in substantially side by side relationship within said housing whereby said projection and imaging paths are substantially adjacent to each other within said housing; and
    said projection and imaging means including lenses having identical magnifications on- and off-axis with said projection means adapted to produce said image off-axis and said imaging means adapted to project the object image on-axis.

* * * * *